United States Patent
Fairley

(10) Patent No.: US 9,724,290 B2
(45) Date of Patent: Aug. 8, 2017

(54) NATURAL SKIN-CARE SERUM

(71) Applicant: Lois Fairley, Chester, VA (US)

(72) Inventor: Lois Fairley, Chester, VA (US)

(73) Assignee: Lois Fairley, Chester, VA (US)

( * ) Notice: Subject to any disclaimer, the term of this patent is extended or adjusted under 35 U.S.C. 154(b) by 210 days.

(21) Appl. No.: 14/724,098

(22) Filed: May 28, 2015

(65) Prior Publication Data

US 2016/0346192 A1 Dec. 1, 2016

(51) Int. Cl.

| | | |
|---|---|---|
| A61K 36/889 | (2006.01) | |
| A61K 36/42 | (2006.01) | |
| A61K 36/33 | (2006.01) | |
| A61K 36/288 | (2006.01) | |
| A61K 8/97 | (2017.01) | |
| A61Q 19/08 | (2006.01) | |
| A61Q 19/00 | (2006.01) | |
| A61K 8/92 | (2006.01) | |

(52) U.S. Cl.
CPC ............... *A61K 8/97* (2013.01); *A61K 8/922* (2013.01); *A61Q 19/00* (2013.01); *A61Q 19/08* (2013.01); *A61K 2800/5922* (2013.01); *A61K 2800/805* (2013.01)

(58) Field of Classification Search
CPC .... A61K 36/889; A61K 36/288; A61K 36/42; A61K 36/33
USPC ......................................... 424/727, 758, 773
See application file for complete search history.

(56) References Cited

U.S. PATENT DOCUMENTS

| | | | | |
|---|---|---|---|---|
| 4,267,852 A | * | 5/1981 | Hullinger | A45D 29/00 132/73 |
| 2006/0134046 A1 | * | 6/2006 | Hanna | A61K 8/31 424/70.13 |

* cited by examiner

*Primary Examiner* — Chris R Tate
*Assistant Examiner* — Deborah Davis

(57) ABSTRACT

A skin care composition for topical use wherein the composition comprises avocado & coconut cream oil, cucumber extract and dandelion root's extract and a method to prepare the composition comprising mixing coconut cream and avocado fruit to make a paste, followed by heating to remove moisture and then extract oil. Mixing the oil obtained with cucumber extract and dandelion extract. The composition is used as anti-aging and moisturizing composition and suitable to all skin types.

4 Claims, No Drawings

NATURAL SKIN-CARE SERUM

CROSS REFERENCE TO RELATED APPLICATION

Not Applicable

FEDERALLY SPONSORED RESEARCH AND DEVELOPMENT

Not Applicable

MICROFICHE APPENDIX

Not Applicable

BACKGROUND OF THE INVENTION (1) Field of Invention

The present invention relates to an organic skin care composition and a method to prepare the composition, wherein the composition is used for topically application and has soothing, anti-aging and, moisturizing properties for people 55 years and older.

(2) Background of Invention

Facial wrinkles, fine surface lines or deeper creases and folds, are all symptoms of skin aging and damage. The symptoms usually appear with increasing age, but may occur early due to certain internal or external factors. Internal factors may include hormonal imbalance, or other physiological factors which may cause premature aging of skin. External factors may include excessive exposure to the sun, high or low temperature, overactive facial expression muscles, frequent use of tobacco products, and poor nutrition. Fine surface wrinkles that progress to deeper creases, deepening facial expression due to repeated skin folding, and deep folds that develop with one's maturity are visible changes which may affect the personality of individual.

Although internal factors may require medical attention and cannot be controlled by an individual, external factors can be, to some extent, taken care off, such as changing the diet plan to get proper nutrition, avoiding direct sun etc. Moreover, some nutrients could be supplied externally to the skin, particularly essential oils that could be easily absorbed through the skin. This may help to prevent any premature ageing or wrinkles and even delay the onset of aging.

Numerous types of topical skin care products are available like cleansers, toners, moisturizers, anti-aging serums, etc. These products usually contain natural oils, medicament, mineral oils, botanicals, bio-peptides etc., and to some extent, help to keep the skin healthy, moisturized and bright. Many attempts have been made to develop formulations that have anti-aging applications. However, most of these formulations contain chemical ingredients that may independently or in combination with other ingredients harm the skin instead of benefiting it, and are, therefore, not suitable for all types of skin. Moreover, these formulations may cause irritation to certain skin types. Apart of this, several invasive techniques are also used in which a medicament is injected or implanted into the areas of skin showing wrinkles or other aging spots. However, invasive techniques have their own risk and require professional expertise, making them costly. Therefore, such techniques are not popular and have been of limited success.

Prior arts disclosing anti-aging compositions include a U.S. Pat. No. 6,551,606 issued to Coty B. V. which discloses a composition having skin regenerative effect; a published PCT/DK1997/000324, which discloses an oil in water emulsion for skin conditioning; a U.S. Pat. No. 8,623,335 issued to "tauna ann Waddington" discloses a composition for treatment of scars and rosacea, and other aspects of skin care. However, the formulations uses synthetic chemicals that may cause several skin problems, such as, dryness and irritation and may not be suitable for all types of skin.

In view of aforesaid problems, there remains a need for new and improved topical skin care compositions that are useful as an anti-aging composition and also provide skin toning and moisturizing without any irritation and is suitable to all skin types. This removes the expense of additional skin care products, which, in turn, eliminates the extra effort and complication associated with using the additional products.

SUMMARY OF THE INVENTION

The present invention discloses a topical skin care composition that has soothing, anti-aging, and moisturizing properties, treating wrinkles, age spots, appearance of fine lines and firmness and does not cause any kind of irritation to skin for people 55 years and over.

Certain embodiments of current invention are to provide a topical skin care composition and is comprised of coconut cream and avocado oil, cucumber extract and dandelion root's extract, and a method to prepare the above composition. The method includes mixing the coconut cream with the ripped avocado fruit, skin removed, to make a paste, followed by heating the paste to remove moisture, and then extracting oil from the residue. After all of this, one mixes the obtained oil with the cucumber and dandelion root's extracts to form the current invention. However, the invention is not limited to these embodiments.

According to another embodiment of current invention, the coconut cream could be obtained from hard brown shell coconuts.

According to another embodiment of current invention, the coconut cream is mixed with avocado fruit flesh and heated to remove the moisture and then extract the oil. Preferably, fresh ripped avocado fruits are used.

According to another embodiment of current invention, cucumber is blended to form liquid which is then filtered to form the extract.

According to another embodiment of current invention, dandelion roots are boiled in water and filtered to form the extract. Preferably, the extract is stored in dark colored bottles to protect it from the light.

According to another embodiment of current invention, the composition could be used for all skin types.

According to another embodiment of current invention, the various components of composition could be in any proportion and quantity.

Thus the present invention provides both a natural skin care composition and a method to prepare such composition.

DETAILED DESCRIPTION OF THE INVENTION

Before explaining at least one embodiment of the invention in detail, it is to be understood that the invention is not limited in its application to the details of construction and the arrangements of the components set forth in the following description. The invention is capable of other embodiments and of being practiced and carried out in various ways. Also it is to be understood that the phraseology and terminology employed herein are for the purpose of description and should not be regarded as limiting.

The present invention provides a topical skin care composition that has soothing, anti-aging and moisturizing properties, and a method to prepare the composition. The composition includes coconut cream and avocado oil 8 cups (5 cups coconut & 2 cups avocado), cucumber extract 1 cup, and dandelion root extract ¾ cups. Whereby, the coconut cream and avocado fruits are blended to form paste, 2 cups of avocado and 4 cups of coconut cream followed by heating (cooking on top of stove in a skillet) for several hours to remove the moisture and then extract the oil. Then, one mixes the oil obtained with the cucumber and dandelion root extracts. Thus, the invention provides a simple and natural composition that doesn't use any synthetic chemicals that irritates the skin. All of the components are very safe for topical application and have positive effects on the skin.

Avocado oil has moisturizing properties. It penetrates the skin and is beneficial to healing processes, and protects the skin from UV rays.

Coconut cream has moisturizing, anti-microbial, anti-bacterial, and anti-fungal properties.

Cucumbers are rich in antioxidants and rejuvenate the skin.

Dandelion root's extract is rich in antioxidants and provide anti-ageing benefits, thus reducing the appearance of fine lines, age spots and wrinkles around the eyes and lips. Besides nourishing the skin, this herb helps tone and firm up sagging and unbalanced skin.

BEST MODE OF CARRYING OUT THE INVENTION

The following are exemplary embodiments of combinations and mixtures of the ingredients discussed in detail above that may be used as working examples of the present composition. In no way should the present composition and method be limited to the examples listed below.

Method of Preparation

Using 2-3 coconuts, meat are extracted from hard-brown coconuts that are cracked open and cut into smaller pieces about 6 cups, using special knife to remove meat. The pieces are blended to get the milk 3½ to 4 cups. The obtained milk is then boiled until the water is evaporated to give coconut cream and oil. The oil is poured off to give the coconut cream that is used in next step.

Ripped avocado fruits (3 fruits) with skin removed were taken into blender and gradually added coconut cream. The mixture is blended till a smooth paste is obtained. The paste is then heated to evaporate the water. While heating, (cook on top of stove on low heat mixing and stirring) care is taken to prevent the paste from burning. After most of the water has evaporated, the residue is collected and thereby oil is extracted from the residue.

Two cucumbers are cut into pieces and taken in a blender. They are blended until a liquid-like mass is obtained, which is then filtered through a cheese cloth to give cucumber extract that is used in composition.

Two cups of dandelion roots are boiled in a quart of water until it boils down to about 3 oz. The Water is strained to a separate container. Another quart of water is then added to the residue and boiled again until water is reduced to 1-2 oz. The extract is collected and stored in dark color bottles to protect it from the light.

After keeping the above components for one-two days, specific quantities of each component, including coconut cream and avocado oil, cucumber extract, and dandelion root's extract are measured and mixed to form the composition. The composition is stored in suitable containers. Using the plastic pipettes (3 ml) to transfer the components, coconut/avocado oil=12 ml is poured into 1 oz. amber glass bottles with eye dropper, combined with 6 ml cucumber extract and 2 ml of dandelion root extract to complete the formula. Time it take to cut, blend and strain and cook milk to get coconut cream is about 6 hours. Then, preparing avocado from removing skin, placing in blender, taking paste and placing the paste in skillet with coconut cream takes about 4 hours. Preparing cucumbers is about 1 hour stored in a glass bottle and refrigerator and the dandelion roots takes about 3 hours from boiling to placing liquid in an amber bottle for storage.

Method of Use

The composition could be applied to skin of face and neck by spreading through hands. The composition could be used in morning and evening.

Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

I claim:

1. A method of preparing a skin care composition comprising the steps of:
   cutting coconut meat into small pieces;
   blending the coconut meat pieces to form a coconut milk;
   evaporating water from the coconut milk;
   separating a coconut oil from the coconut milk to form a coconut cream;
   blending the coconut cream with avocado fruit flesh to form a coconut-avocado smooth paste;
   evaporating water from the smooth paste to form an evaporated smooth paste;
   extracting oil from the evaporated smooth paste to form a smooth paste oil;
   blending cucumber to form a cucumber liquid;
   boiling dandelion roots in water to obtain a dandelion root extract; and
   mixing the smooth paste oil, the cucumber liquid, and the dandelion root extract to obtain said skin care composition.

2. The method according to claim 1, wherein the coconut meat is obtained from hard brown shell coconuts.

3. The method according to claim 1, wherein the avocado fruit flesh is obtained from ripe avocados.

4. The method according to claim 1, wherein the dandelion root extract has been stored in a dark colored bottle to protect it from light.

* * * * *